United States Patent [19]

Hohberg et al.

[11] Patent Number: 4,919,535

[45] Date of Patent: Apr. 24, 1990

[54] REFLECTANCE MEASURING APPARATUS FOR MAKING CONTACTLESS MEASUREMENTS

[75] Inventors: Gerhard Hohberg, Aalen-Dewangen; Hermann Gerlinger, Aalen-Ebnat, both of Fed. Rep. of Germany

[73] Assignee: Carl-Zeiss-Stiftung, Heidenheim, Fed. Rep. of Germany

[21] Appl. No.: 147,226

[22] Filed: Jan. 22, 1988

[30] Foreign Application Priority Data

Jan. 22, 1987 [DE] Fed. Rep. of Germany ....... 3701721

[51] Int. Cl.$^5$ ...................... G01N 21/86; G01N 21/47
[52] U.S. Cl. ..................... 356/429; 356/446
[58] Field of Search ............... 356/446, 448, 429, 430, 356/319; 250/571

[56] References Cited

U.S. PATENT DOCUMENTS

| | | | |
|---|---|---|---|
| 3,526,777 | 9/1970 | Robinson | 250/237 |
| 3,718,399 | 2/1973 | Kalman | 356/446 |
| 3,910,701 | 10/1975 | Henderson et al. | 356/446 |
| 3,999,864 | 12/1976 | Mutter | 250/227 |
| 4,003,660 | 1/1977 | Christie et al. | 356/448 |
| 4,022,534 | 5/1977 | Kishner | 356/446 |
| 4,029,420 | 6/1977 | Simms | 356/446 |
| 4,076,421 | 2/1978 | Kishner | 356/446 |
| 4,101,222 | 7/1978 | Mathisen | 356/446 |
| 4,379,225 | 4/1983 | Apothaker | 250/227 |
| 4,464,054 | 8/1984 | Karras et al. | 356/446 |
| 4,568,191 | 2/1986 | Barry | 356/446 |
| 4,583,858 | 4/1986 | Lebling et al. | 356/446 |
| 4,632,559 | 12/1986 | Brunsling | 356/446 |
| 4,676,653 | 6/1987 | Strohmeier et al. | 356/446 |
| 4,756,619 | 7/1988 | Gerlinger et al. | 356/446 |
| 4,770,530 | 9/1988 | Van Aken et al. | 356/448 |

FOREIGN PATENT DOCUMENTS

| | | |
|---|---|---|
| 0099024 | 1/1984 | European Pat. Off. . |
| 1902101 | 1/1971 | Fed. Rep. of Germany . |
| 8417621 | 2/1986 | Fed. Rep. of Germany . |
| 2066452 | 7/1981 | United Kingdom . |

OTHER PUBLICATIONS

Conrad et al, "Spectrophotometer Head With Variable Spot Size", IBM Technical Disclosure Bulletin, vol. 20, No. 3 (Aug. 1977).
Patent Abstracts of Japan: vol. 9, No. 129 (P-361) (1852), 5 Jun. 85 and JP-A-60014132 (Kawasaki Seitetsu K.K.), 24.01.85.

Primary Examiner—Richard A. Rosenberger
Attorney, Agent, or Firm—Walter Ottesen

[57] ABSTRACT

The invention is directed to a reflectance measuring apparatus for making contactless measurements on structured test objects wherein the measuring result is independent of the distance of the test object within a difference range (d). The illumination arrangement and the measuring arrangement have a common center axis (z) which extends perpendicularly to the surface of the test object. At least the illumination arrangement or the measuring arrangement includes at least three radiation transmitters or three radiation receivers having optical axes arranged on at least one cone (c) concentric with respect to the common center axis (z). Of the set of radiation transmitters and the set of radiation receivers, one of the sets is configured to have a parallel ray bundle with a core area (k) and the other one of the sets is configured to have a bundle having a limited aperture with the area (m) covered by the limited aperture or apertures being smaller than the core area (k) within a distance range (d).

27 Claims, 5 Drawing Sheets

REFLECTANCE MEASURING APPARATUS FOR MAKING CONTACTLESS MEASUREMENTS

FIELD OF THE INVENTION

The invention relates to a reflectance measuring apparatus for contactless measurement such as on a moving band. The apparatus includes an illumination arrangement for illuminating an irradiated area on the surface of the test object and includes a measuring arrangement for detecting the radiation reflected from a measuring area of the surface of the test object.

BACKGROUND OF THE INVENTION

An apparatus of the kind referred to above is disclosed in U.S. Pat. No. 3,458,261. In this apparatus, a small region of a moving band is illuminated by a pulsed light source and an image of a diaphragm illuminated by the light source is formed on the band. U.S. Pat. No. 3,458,261 refers to this irradiated area as being a field limiting image. An image of a middle zone of this irradiated area is formed on a receiver, so that the measuring area from which the reflected radiation is detected by the measuring device is smaller than the irradiated area. This known apparatus has the disadvantage that the measurement result is dependent on the distance between the band and the measuring device. In many machines in which the reflectance or the color of moving bands must be measured, however, this distance is not constant, because at the locations where it is possible to accommodate a measuring device, the band flutters.

The known arrangement further has the disadvantage that it is not suitable for structured samples such as textiles because with test objects of this kind, the measurement result is dependent upon azimuth, that is, it is dependent on the orientation of the sample with respect to the measuring apparatus.

SUMMARY OF THE INVENTION

Accordingly, it is an object of the invention to provide a reflectance measuring apparatus in which the result of measurement is not influenced by the distance of the sample from the measuring apparatus within a predetermined difference region. It is another object of the invention to provide such a reflectance measuring apparatus wherein the structure of the sample has virtually no influence on the measuring result.

The reflectance measuring apparatus includes an illuminating arrangement and a measuring arrangement having a common center axis which is perpendicular to the surface of the test object. The illuminating arrangement or the measuring arrangement include at least three radiation transmitters or radiation receivers having respective optical axes arranged on at least one concentric cone around the center axis. If the radiation transmitters are configured to have a parallel bundle of rays with a core area, then the radiation receivers are configured to have a bundle with a limited aperture. On the other hand, if the radiation transmitters are configured to have a bundle with a limited aperture, then the radiation receivers are configured to have a parallel radiation bundle with a core region. The region detected by the limited aperture or the limited apertures on the surface of the test object is smaller than the core area within a distance range.

In an especially advantageous embodiment of the invention, an uneven number of radiation transmitters or radiation receivers are arranged on the cone or cones to have the same azimuth angles with respect to each other.

In another advantageous embodiment of the invention, the radiation transmitters or the radiation receivers, which are configured to have a bundle with a limited aperture, are comprised of light conductors and their respective end faces. In still another advantageous embodiment, the radiation transmitters or radiation receivers are made of lenses and limiting surfaces with the limiting surfaces being defined by the end faces of light conductors.

In a likewise advantageous embodiment of the invention, the radiation transmitters or radiation receivers, which are configured to have a parallel ray bundle with a core area, are comprised of light conductors having repective end faces arranged in the focus of condensers. If only one radiation transmitter is utilized, then the light source can also be arranged in the focus of a condenser.

BRIEF DESCRIPTION OF THE DRAWINGS

The invention will now be described with reference to the drawings wherein:

FIG. 2b is a schematic plan view of the illuminating head and measuring head shown in FIG. 2a.

DESCRIPTION OF THE PREFERRED EMBODIMENTS OF THE INVENTION

Figure 1:
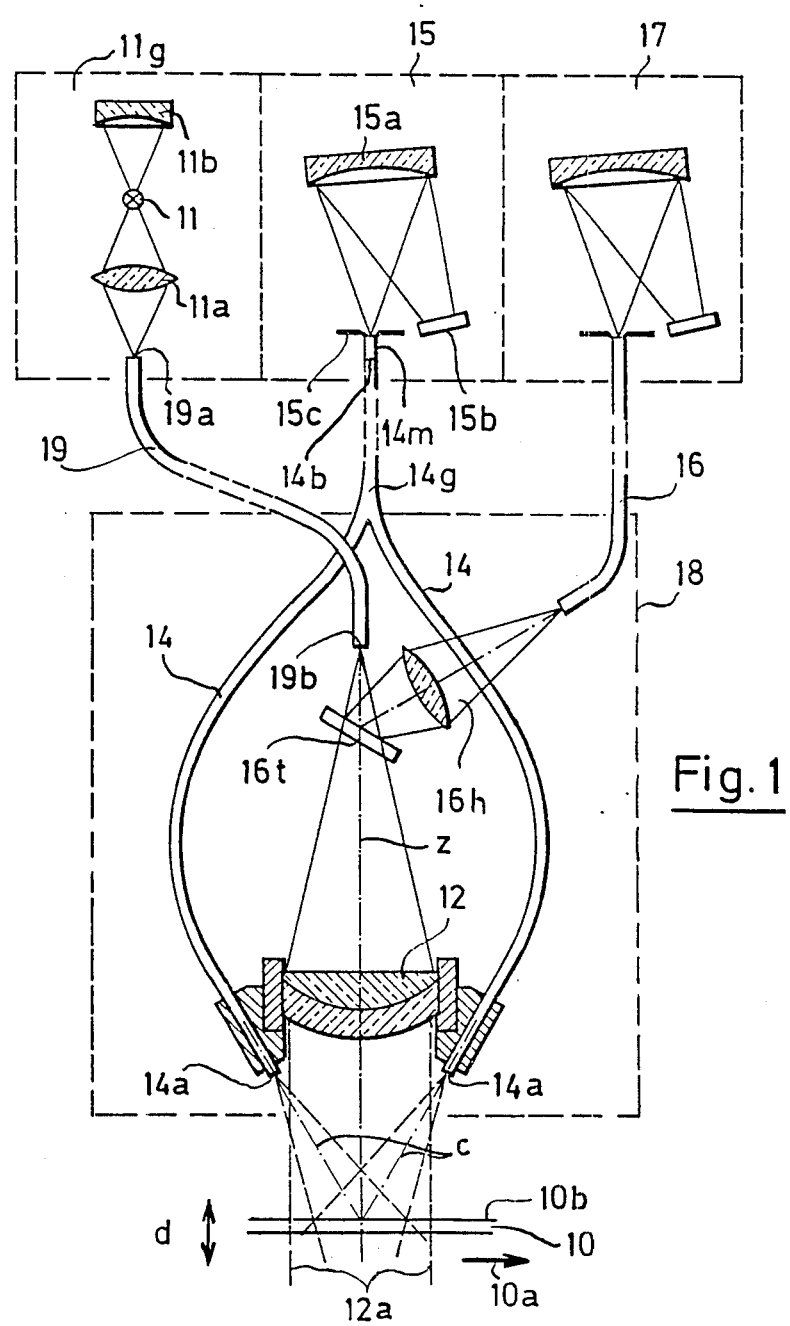
FIG. 1 is a schematic showing a first embodiment of the reflectance measuring apparatus according to the invention.

FIG. 1 shows a moving band 10 such as that associated with a paper or printing machine. The band 10 is moved in the direction of the arrow 10a. Its surface 10b moves up and down by a few millimeters in the range (d); that is, the band flutters at the locations where there is space to accommodate a measuring device or measuring head 18 for determining the reflectance capacity or the color values. This changing distance between the measuring head 18 and the surface 10b influences the reflection values and color values for known measuring arrangements up to a multiple of what the human eye can realize as a difference.

In the embodiment of FIG. 1, the surface 10b of the test object is illuminated via the light conductor 19. The light source 11 is imaged on the entrance face 19a of the light conductor 19 by the lens 11a. A suitable light source is preferably a short-arc discharge lamp such as an XBO 75 of the Osram Company. If the strip moves quickly, then a flash lamp such as BGS 2902Z of the Heimann Company is especially well suited because it makes short measuring times possible. Both the Osram Company and the Heimann Company are firms organized and doing business in the Federal Republic of Germany.

Discharge lamps of the type referred to above mostly show a non-uniform change of the arc position by means of which the illumination of the entrance face 19a is changed. This effect is minimized by the concave mirror 11b which images the arc within itself. When the arc deviates, then the mirror image thereof wanders in the opposite direction so that a more even illumination in total results. The lens 11a can be configured with an aspherical surface to obtain a more uniform illumination of the entrance face 19a. Here, as at all other locations, an individual fiber, several individual fibers or a multiplicity of individual fibers can be utilized as a light conductor.

Figure 2A:
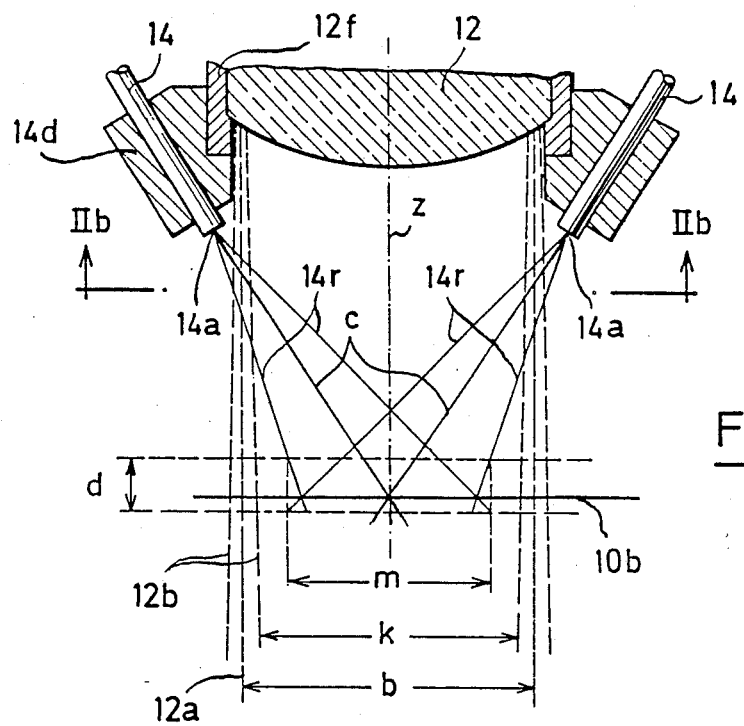
FIG. 2a is a detail schematic showing the geometric relationships between the illuminating head and the measuring head and the test-object surface for the embodiment according to FIG. 1.

The exit face 19b of the light conductor 19 is mounted in the focal point of the condenser 12. If the exit face 19b were a point, then an exact parallel light bundle having the boundary lines 12a would be formed after the condenser 12 provided that the imaging errors of the condenser would be considered as being negligible. The actual relationships are illustrated in FIG. 2a in an enlarged scale. The part of the surface 10b of the test object illuminated by the boundary lines 12a is designated as the irradiation surface (b). However, a divergence results because of the expansion of the exit face 19b which causes a distance-dependent sown edge between the lines identified by reference numeral 12b. However, the ideal conditions remain fulfilled within a core area (k) so that in this area, the illumination intensity of the surface of the test object is not dependent upon the distance of this surface 10b from the measuring head 18.

Figure 2B:
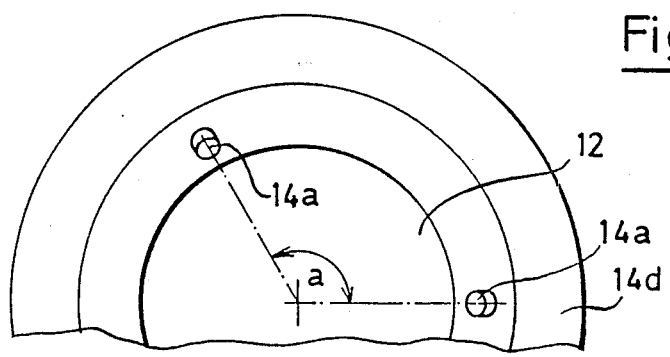

The radiation returned from the surface 10b of the test object is detected in part by radiation receivers which comprise the entrance faces 14a of the light conductors 14 for the embodiment shown in FIGS. 1 to 2b. These light conductors are mounted so that they lie with the respective optical axes of their entrance faces 14a on a cone (c). The center axis (z) of the cone (c) is coincident with the center axis of the illumination arrangement and the vertex of the cone (c) lies in the surface 10b of the test object.

The aperture of the light conductor having the boundary rays 14r limits the measuring surfaces on the surface 10b of the test object. If the distance of the surface 10b changes by an amount (d), then the measuring surfaces remain in the measuring area designated by reference letter (m) in FIG. 2a. This measuring area (m) lies within the core area of the irradiation surface designated with reference letter (k) and it is within this core area that the intensity of illumination is independent of the distance to the surface of the test object as described above. Since this measuring area (m) lies within the core area (k), the component of the returned radiation also remains independent of the distance of the surface of the test object because of the constant aperture and therefore because of the constant spatial angle for the detected radiation. This component of returned radiation remains independent of the distance of the surface of the test object so long as the given difference range (d) is not exceeded.

The necessary limitation of the spatial angle or the aperture does not have to occur through the entrance faces 14a of the fibers 14. This limitation can also be achieved with the aid of diaphragms at the output of the fibers since the inclination angles in the fibers are maintained.

For test objects without structure, one radiation receiver is basically possible. Several radiation receivers are required for structured test objects. Since structured test objects such as textiles most often have two symmetrical axes perpendicular to each other, it is especially advantageous to provide an uneven number of radiation receivers which have the same azimuth angle (a) with respect to each other. FIG. 2b is a plan view looking down on the illuminating head and measuring head 18 and shows this arrangement for three radiation receivers. In this case, the azimuth angle (a) is 120°. If a larger number of radiation receivers is provided, then their number can also be an even number.

It is preferable to fix the light conductors 14 in a rotational part 14d which can be fitted on the frame 12f of the condenser 12.

The light conductors 14 are preferably united to form a common light conductor 14g while still in the measuring head 18 and are then led to a diode-array spectrometer 15. A diode array spectrometer of the type identified by reference numeral 15 is disclosed, for example, in U.S. Pat. No. 4,598,715 and comprises a holographic concave grating 15a and the diode array 15b. The entrance slit 15c is illuminated through the end 14b of the light conductor 14g. Since the light conductor comprises several light conducting fibers, it is preferable to insert a glass rod 14m as a light mixer between the light conductor end 14b and the slit 15c so that all individual fibers contribute by the same amount to the measured value.

Especially if a pulse light source is utilized for the light source 11, it is necessary to record the spectrum of each pulse as a comparison. For this purpose, a divider plate 16t is mounted in the illumination beam path as shown in FIG. 1 with which a component of the illuminating light is coupled into the light conductor 16 via the lens 16h. The light conductor 16 leads to a second diode-array spectrometer 17. The evaluation of the spectra received from the spectrometers and the computation of the reflected values and color values is performed in a known manner.

It is preferable to combine the illumination arrangement and the measuring arrangement 18 as a measuring head in one housing which is connected via respective light conductors (14, 16 and 19) with the spectrometers (15 and 17) and the lamp housing 11g. It is furthermore advantageous to arrange the measuring head 18 with a pivot arrangement (not shown) above the strip 10 so that a color or white standard can be measured for the purposes of calibration when the measuring head 18 is pivoted out.

Figure 3:
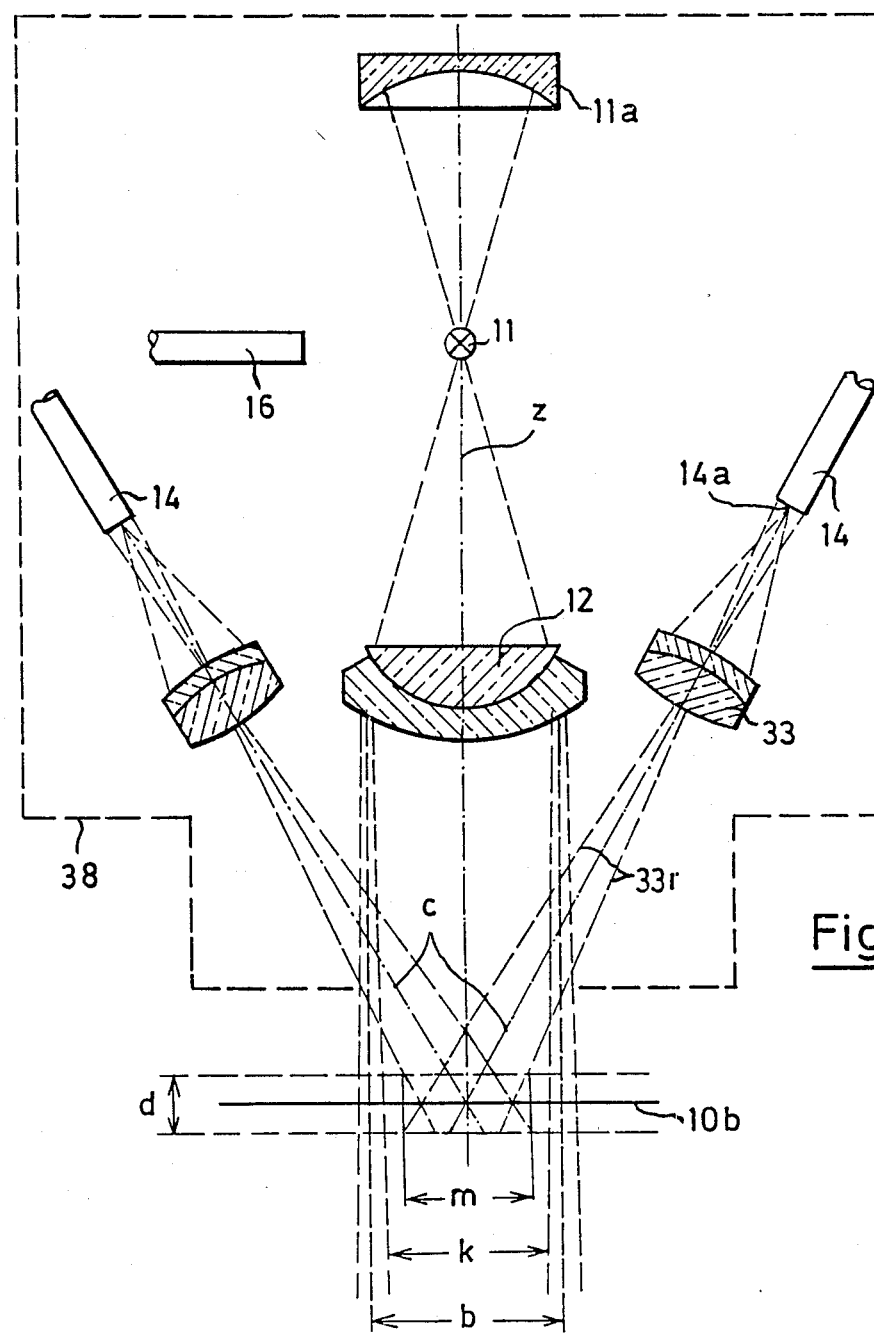
FIG. 3 is a schematic representation of a second embodiment of the reflectance measuring apparatus according to the invention.

FIG. 3 shows a further embodiment of the invention wherein the light source 11 is mounted in the measuring head 38. In this embodiment, the light source 11 is located directly in the focus of the condenser 12. What was stated above for the irradiation area (b) and the core area (k) corresponds to this embodiment and likewise for the concave mirror 11a.

FIG. 3 further shows another embodiment for the radiation receivers which can be combined with the illumination arrangement of FIG. 1. A two-lens objective 33 is utilized with this radiation receiver in order to obtain the best possible correction especially of the chromatic imaging error. The objective 33 need not provide a sharp image of the surface 10b of the strip 10 on the input face 14a of the light conductor 14; instead, its essential task is that it together with the input face 14a limit the magnitude of the measuring surface (m) on the surface on the test object. This can be varied by means of varying the distance of the objective 33 from the surface 10b of the strip. Here too, the measuring surface (m) must always be within the core area (k) of the irradiated surface (b) for a difference range (d). Another limiting surface can be substituted for the input face 14a and it is only important that the aperture be constant, that is, that the spatial angle detected by the radiation receiver be constant and thereby be independent of the distance between the surface 10b of the strip and the illuminating and measuring arrangement 38.

As in FIG. 1, the light conductors 14 in this embodiment are combined into a common light conductor and they illuminate the entrance slit 15c of the diode-array spectrometer 15. Likewise, a component of the illuminating light is conducted via light conductor 16 to a second diode-array spectrometer 17 for comparison measurement.

Figure 4:
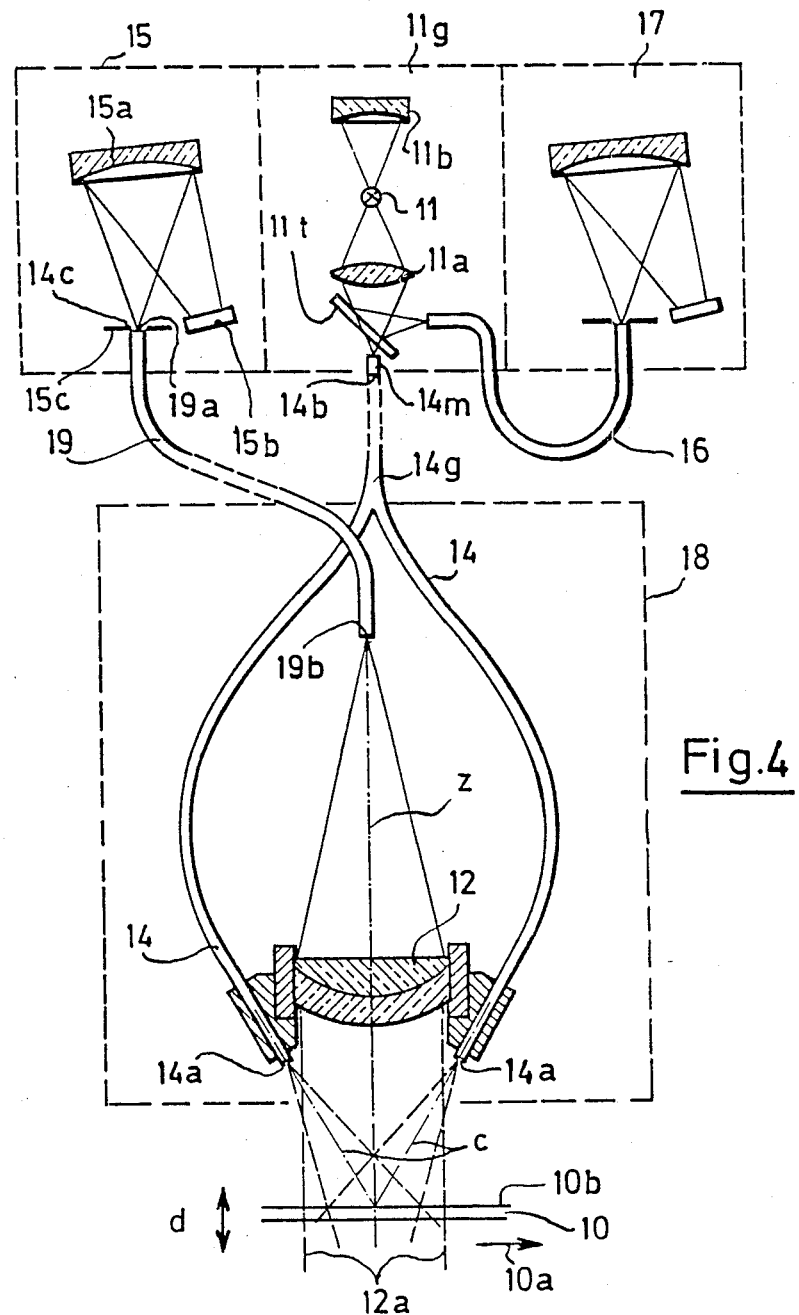
FIG. 4 is a schematic showing the arrangement of FIGS. 1 to 2b wherein, however, the illuminating and the reflecting rays are exchanged with each other.

In the embodiments shown in FIGS. 1 to 3, the illuminating and the returned (detected) rays can be exchanged with each other in the measuring head (18, 38). This is explained with reference to FIG. 4. In FIG. 4, the light conductors 14 are connected with the lamp housing 11g and the light conductor 19 is connected with the diode-array spectrometer 15 so that the illumination is concentric and the reflected measurement occurs perpendicularly to the surface 10b of the test object with the measuring head being otherwise the same. The reference radiation is diverted in the lamp housing 11g via the divider plate 11t.

Also in this embodiment, the result of the reflection measurement is independent of the distance of the surface of the test object within the difference range (d) so long as the surface (m) is smaller than the core area (k) for the radiation receivers (12, 19b), the surface (m) being the surface within which an illumination is provided.

It is by no means necessary that the parallel bundle of rays lie in the center axis (z) as shown in FIGS. 1 to 4. Instead, a bundle having a limited aperture can also lie in the center axis (z); then, several radiation transmitters or radiation receivers having a parallel ray bundle will lie on the cone (c).

Several radiation transmitters together with several radiation receivers can also be utilized. These transmitters and receivers can lie on a common cone (c) or on two different cones having the same axis and the same vertex. In this instance, the number of radiation transmitters can be different than the number of radiation receivers.

Figure 5:
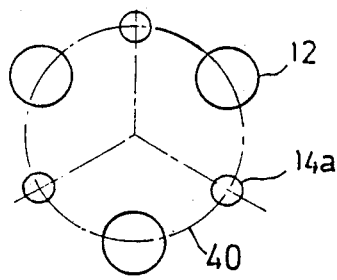
FIG. 5 is a schematic plan view of the illuminating head and measuring head wherein all of the radiation transmitters and all of the radiation receivers are arranged on a common conical surface.
Figure 6:
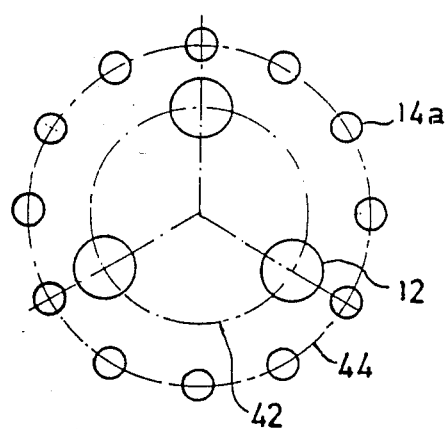
FIG. 6 is a schematic plan view of the illuminating head and measuring head wherein the radiation transmitters are all disposed on a first conical surface and the radiation receivers are all mounted on a second conical surface; and, FIG. 7 is a schematic representation of the illuminating head and measuring head wherein the radiation transmitters and radiation receivers are distributed onto two conical surfaces.

The schematic plan view of FIG. 5 shows an embodiment where all of the radiation transmitters 12 and all of the radiation receivers 14a are arranged on a common conical surface 40. In FIG. 6, a schematic plan view is shown of an embodiment wherein the radiation transmitters 12 are all disposed on a first conical surface 42 and all the radiation receivers 14a are all mounted on a second conical surface 44.

Finally, it is also possible to arrange the radiation transmitters or the radiation receivers or both respectively on several different cones. However, for structured test objects, at least three radiation transmitters or radiation receivers are needed on each cone.

Figure 7:
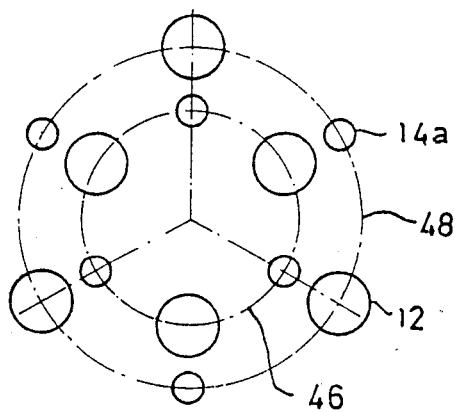

Thus, FIG. 7 is a plan schematic view of the illuminating head and measuring head according to an embodiment wherein only selected ones of the radiation transmitters 12 are arranged on a first conical surface 46 and the remaining ones of the radiation transmitters 12 are arranged on a second conical surface 48. Similarly, selected ones of the radiation receivers 14a are arranged on the first conical surface 46 whereas the remaining ones of the radiation receivers 14a are arranged on the second conical surface 48.

It is understood that the foregoing description is that of the preferred embodiments of the invention and that various changes and modifications may be made thereto without departing from the spirit and scope of the invention as defined in the appended claim.

What is claimed is:

1. A reflectance measuring apparatus for making contactless measurements on a surface of a structured sample moving in a given direction past the apparatus and disposed at a spacing from the apparatus, the level of the surface of the sample fluttering within a predetermined distance range (d) by which said spacing is increased or decreased, the apparatus comprising:

an illuminating device disposed at an optically unobstructed spacing from the sample for illuminating an irradiated area on said surface of the sample;

a measuring device for detecting radiation reflected from said surface;

said illuminating device and said measuring device conjointly defining a common central axis transverse to said surface;

said measuring device including at least three radiation receivers having respective optical axes and mounted to cause said optical axes to lie on at least one conical surface concentric with said central axis with each two mutually adjacent ones of said receivers being spaced from each other by a predetermined azimuth angle whereby the contactless measurement is independent of the orientation of the structured sample with respect to said measuring apparatus;

said illuminating device including parallel beam means for producing and directing a bundle of parallel illuminating rays onto said surface so as to define an optically unobstructedly illuminated core area (k) wherein the intensity of illumination is independent of the spacing of said surface from said illumination device within said distance range (d); and, said radiation receivers including aperture means for limiting the bundle of said rays detected by said receivers to those rays which are received in a spatial angle defining a detected region (m) on said surface smaller than said core area (k) for movements of said sample within said predetermined distance range (d), said spatial angle being constant thereby causing the received radiation to be independent of said spacing so long as the movement of said sample remains within said distance range (d).

2. The reflectance measuring apparatus of claim 1, said radiation receivers being an uneven number and being arranged on said conical surface so as to cause each two mutually adjacent ones of said receivers to conjointly define the same azimuth angle (a).

3. The reflectance measuring apparatus of claim 1, said radiation receivers each comprising a light conductor having an end face for receiving rays from within said detected region.

4. The reflectance measuring apparatus of claim 1, said radiation receivers each comprising a lens and a limiting surface for receiving rays from within said detected region.

5. The reflectance measuring apparatus of claim 1, said illuminating device comprising a light source for generating illuminating light; light conductor means for conducting said illuminating light away from said light source and defining a light emitting end face; and, a condenser mounted adjacent said surface and defining a focus containing said light emitting end face.

6. The reflectance measuring apparatus of claim 1, said illuminating device comprising a condenser mounted adjacent said surface and defining a focus; and, a light source mounted in said focus.

7. The reflectance measuring apparatus of claim 1, wherein said illuminating device includes a light source and light transmitting means for transmitting illuminating light rays to said parallel beam means; and, the apparatus further comprising a reference measuring arrangement including a divider means for dividing a component beam out of said illuminating light rays; a diode-array spectrometer; and, light-conducting means for conducting said component beam to said diode-array spectrometer.

8. The reflectance measuring apparatus of claim 1, said apparatus being pivotally mounted for pivoting the same away from said sample, the combination of a color or white standard pivotally mounted so as to be pivoted into position at an elevation corresponding to the mean value of said predetermined distance range (d).

9. The reflectance measuring apparatus of claim 1, said illuminating device including a light source for transmitting light to said parallel beam means, said light source being a pulse light source.

10. A reflectance measuring apparatus for making contactless measurements on a surface of a structured sample moving in a given direction past the apparatus and disposed at a spacing from the apparatus, the level of the surface of the sample fluttering within a predetermined distance range (d) by which said spacing is increased or decreased, the apparatus comprising:

an illuminating device disposed at an optically unobstructed spacing from the sample for illuminating an irradiated area on said surface of the sample;

a measuring device for detecting radiation reflected from said surface;

said illuminating device and said measuring device conjointly defining a common central axis transverse to said surface;

said measuring device including at least three radiation receivers having respective optical axes and mounted to cause said optical axes to lie on at least one conical surface concentric with said central axis with each two mutually adjacent ones of said receivers being spaced from each other by a predetermined azimuth angle whereby the contactless measurement is independent of the orientation of the structured sample with respect to said measuring apparatus;

said illuminating device including parallel beam means for producing and directing a bundle of parallel illuminating rays onto said surface so as to define an optically unobstructedly illuminated core area (k) wherein the intensity of illumination is independent of the spacing of said surface from said illumination device within said distance range (d);

said radiation receivers being respective light conductors and including aperture means for limiting the bundle of said rays detected by said receivers to those rays which are received in a spatial angle defining a detected region (m) on said surface smaller than said core area (k) for movements of said sample within said predetermined distance range (d), said spatial angle being constant thereby causing the received radiation to be independent of said spacing so long as the movement of said sample remains within said distance range (d);

a measuring head containing said radiation receivers therein; and, light evaluation means for receiving the rays reflected from said detected region (m); and, said light conductors being connected to said light evaluation means.

11. The reflectance measuring apparatus of claim 10, said light evaluation means being a diode-array spectrometer.

12. A reflectance measuring apparatus for making contactless measurements on a surface of a structured sample moving in a given direction past the apparatus and disposed at a spacing from the apparatus, the level of the surface of the sample fluttering within a predetermined distance range (d) by which said spacing is increased or decreased, the apparatus comprising:

an illuminating device disposed at an optically unobstructed spacing from the sample for illuminating an irradiated area on said surface of the sample;

a measuring device for detecting radiation reflected from said surface;

said illuminating device and said measuring device conjointly defining a common central axis transverse to said surface;

said illuminating device including at least three radiation transmitters having respective optical axes and mounted to cause said optical axes to lie on at least one conical surface concentric with said central axis and so as to define an illuminated area (m) on said surface with each two mutually adjacent ones of said transmitters being spaced from each other by a predetermined azimuth angle whereby the contactless measurement is independent of the orientation of the structured sample with respect to said measuring apparatus;

said measuring device including parallel beam means for receiving a bundle of parallel reflected rays from a core area (k) on said surface; and, said radiation transmitters including aperture means for limiting the bundle of said rays transmitted by said transmitters to those rays which are transmitted in a spatial angle to an illuminated region (m) on said surface smaller than said core area (k) for movements of said sample within said predetermined distance range (d), said spatial angle being constant thereby causing the transmitted rays to be independent of said spacing so long as the movement of said sample remains within said distance range (d).

13. The reflectance measuring apparatus of claim 12, said radiation transmitters being an uneven number and being arranged on said conical surface so as to cause each two mutually adjacent ones of said transmitters to conjointly define the same azimuth angle (a).

14. The reflectance measuring apparatus of claim 12, said radiation transmitters each comprising a light conductor having an end face for transmitting rays in said spatial angle to said illuminated region (m).

15. The reflectance measuring apparatus of claim 12, said radiation transmitters each comprising a lens and a limiting surface transmitting rays in said spatial angle to said illuminated region (m).

16. The reflectance measuring apparatus of claim 12, said measuring device comprising: light conductor means for conducting said receiving rays away from said parallel beam means and defining a light receiving end face; and, said parallel beam means including a condenser mounted adjacent said surface and defining a focus containing said light receiving end face.

17. The reflectance measuring apparatus of claim 12, wherein said illuminating device includes a light source and light transmitting means for transmitting illuminating light rays to said radiation transmitters; and, the apparatus further comprising a reference measuring arrangement including a divider means for dividing a component beam out of said illuminating light rays; a diode-array spectrometer; and, light-conducting means for conducting said component beam to said diode-array spectrometer.

18. The reflectance measuring apparatus of claim 12, said apparatus being pivotally mounted for pivoting the same away from said sample, the combination of a color or white standard pivotally mounted so as to be pivoted into position at an elevation corresponding to the mean value of said predetermined distance range (d).

19. The reflectance measuring apparatus of claim 12, said illuminating device including a light source for transmitting light to said radiation transmitters, said light source being a pulse light source.

20. A reflectance measuring apparatus for making contactless measurements on a surface of a structured sample moving in a given direction past the apparatus and disposed at a spacing from the apparatus, the level of the surface of the sample fluttering within a predetermined distance range (d) by which said spacing is increased or decreased, the apparatus comprising:

an illuminating device disposed at an optically unobstructed spacing from the sample for illuminating an irradiated area on said surface of the sample;

a measuring device for detecting radiation reflected from said surface;

said illuminating device and said measuring device conjointly defining a common central axis transverse to said surface;

said illuminating device including at least three radiation transmitters having respective optical axes and mounted to cause said optical axes to lie on at least one conical surface concentric with said central axis and so as to define an illuminated area (m) on said surface with each two mutually adjacent ones of said transmitters being spaced from each other by a predetermined azimuth angle whereby the contactless measurement is independent of the orientation of the structured sample with respect to said measuring apparatus;

said measuring device including parallel beam means for receiving a bundle of parallel reflected rays from a core area (k) on said surface; and, said radiation transmitters including aperture means for limiting the bundle of said rays transmitted by said transmitters to those rays which are transmitted in a spatial angle to an illuminated region (m) on said surface smaller than said core area (k) for movements of said sample within said predetermined distance range (d), said spatial angle being constant thereby causing the transmitted rays to remain within said core area (k) independently of said spacing so long as the movement of said sample remains within said distance range (d)

a measuring head containing said measuring device therein; and, light evaluation means for receiving the rays reflected from said detected region k; and, a light conductor for connecting said measuring device to said light evaluation means.

21. The reflectance measuring apparatus of claim 20, said light evaluation means being a diode-array spectrometer.

22. A reflectance measuring apparatus for making contactless measurements on a surface of a sample, the level of the surface of the sample varying within a predetermined distance range (d), the apparatus comprising:

an illuminating device for illuminating an irradiated area on said surface of the sample;

a measuring device for detecting radiation reflected from said surface;

said illuminating device and said measuring device conjointly defining a common central axis transverse to said surface;

said illuminating device including parallel beam means for directing a bundle of parallel illuminating rays to said surface; said illuminating device further including a plurality of radiation transmitters for transmitting respective bundles of said illuminating rays onto said surface, said radiation transmitters having respective illuminating optical axes and being mounted to cause said optical axes to lie on a conical surface concentric with said central axis and so as to conjointly define an illuminated core area (k) on the surface of the sample;

said measuring device including a plurality of radiation receivers having respective receiving optical axes and mounted so as to cause said receiving optical axes to also lie on said conical surface; and, said radiation receivers including aperture means for limiting the bundle of said rays detected by said receivers to a detected region (m) on said surface smaller than said core area (k) within said predetermined distance range (d).

23. A reflectance measuring apparatus for making contactless measurements on a surface of a sample, the level of the surface of the sample varying within a predetermined distance range (d), the apparatus comprising:

an illuminating device for illuminating an irradiated area on said surface of the sample;

a measuring device for detecting radiation reflected from said surface;

said illuminating device and said measuring device conjointly defining a common central axis transverse to said surface;

said illuminating device including parallel beam means for directing a bundle of parallel illuminating rays to said surface; said illuminating device further including a plurality of radiation transmitters for transmitting respective bundles of said illuminating rays onto said surface, said radiation transmitters having respective illuminating optical axes and being mounted to cause said optical axes to lie on a first conical surface concentric with as to conjointly define an area (k) on the surface of the sample;

said measuring device including a plurality of radiation receivers having respective receiving optical axes and mounted so as to cause said receiving optical axes to lie on a second conical surface concentric with said central axis and said first conical surface;

said first and second conical surfaces having a common vertex in the region of the surface of the sample; and, said radiation receivers including aperture means for limiting the bundle of said rays detected by said receivers to a detected region (m) on said surface smaller than said core area (k) within said predetermined distance range (d).

24. A reflectance measuring apparatus for making contactless measurements on a surface of a sample, the level of the surface of the sample varying within a predetermined distance range (d), the apparatus comprising:

an illuminating device for illuminating an irradiated area on said surface of the sample;

a measuring device for detecting radiation reflected from said surface;

said illuminating device and said measuring device conjointly defining a common central axis transverse to said surface;

an imaginary first conical surface concentric with said central axis and an imaginary second conical surface also concentric with said central axis;

said illuminating device including parallel beam means for directing a bundle of parallel illuminating rays to said surface; said illuminating device further including a plurality of radiation transmitters for transmitting respective bundles of said illuminating rays onto said surface, said radiation transmitters having respective illuminating optical axes with selected ones of said transmitters being mounted to cause the optical axes corresponding thereto to lie on said first conical surface while the remaining ones of said transmitters are mounted so as to cause the optical axes thereof to lie on said second conical surface; said first and second conical surfaces having a common vertex in the region of the surface of the sample and said transmitters conjointly defining an illuminated core area (k) on the surface of the sample;

said measuring device including a plurality of radiation receivers having respective receiving optical axes with selected ones of said receivers being mounted to cause the optical axes corresponding thereto to lie on said first conical surface while the remaining ones of said receivers are mounted so as to cause the optical axes thereof to lie on said second conical surface; and, said radiation receivers including aperture means for limiting the bundle of said rays detected by said receivers to a detected region (m) on said surface smaller than said core area (k) within said predetermined distance range (d).

25. A reflectance measuring apparatus for making contactless measurements on a surface of a sample, the level of the surface of the sample varying within a predetermined distance range (d), the apparatus comprising:

an illuminating device for illuminating an irradiated area on said surface of the sample;

a measuring device for detecting radiation reflected from said surface;

said illuminating device and said measuring device conjointly defining a common central axis transverse to said surface;

said illuminating device including at least three radiation transmitters for transmitting respective bundles of illuminating rays onto said surface, said radiation transmitters having respective illuminating optical axes and being mounted to cause said optical axes to lie on a conical surface concentric with said central axis and so as to conjointly define an illuminated area (m) on the surface of the sample;

said measuring device including a plurality of radiation receivers having respective receiving optical axes and mounted so as to cause said receiving optical axes to also lie on said conical surface; each of said receivers including parallel beam means for receiving a bundle of parallel reflected rays from a core area (k) on said surface; and, said radiation transmitters including aperture means for limiting the bundle of said rays transmitted by said transmitters to an illuminated region (m) on said surface smaller than said core area (k) within said predetermined distance range (d).

26. A reflectance measuring apparatus for making contactless measurements on a surface of a sample, the level of the surface of the sample varying within a predetermined distance range (d), the apparatus comprising:

an illuminating device for illuminating an irradiated area on said surface of the sample;

a measuring device for detecting radiation reflected from said surface;

said illuminating device and said measuring device conjointly defining a common central axis transverse to said surface;

said illuminating device including at least three radiation transmitters for transmitting respective bundles of illuminating rays onto said surface, said radiation transmitters having respective illuminating optical axes and being mounted to cause said optical axes to lie on a first conical surface concentric with said central axis and so as to conjointly define an illuminated area (m) on the surface of the sample;

said measuring device including a plurality of radiation receivers having respective receiving optical axes and mounted so as to cause said receiving optical axes to lie on a second conical surface concentric with said central axis and said first conical surface; each of said receivers including parallel beam means for receiving a bundle of parallel reflected rays from a core area (k) on said surface; and, said radiation transmitters including aperture means for limiting the bundle of said rays transmitted by said transmitters to an illuminated region (m) on said surface smaller than said core area (k) within said predetermined distance range (d).

27. A reflectance measuring apparatus for making contactless measurements on a surface of a sample, the level of the surface of the sample varying within a predetermined distance range (d), the apparatus comprising:
- an illuminating device for illuminating an irradiated area on said surface of the sample;
- a measuring device for detecting radiation reflected from said surface;
- said illuminating device and said measuring device conjointly defining a common central axis transverse to said surface;
- an imaginary first conical surface concentric with said central axis and an imaginary second conical surface also concentric with said central axis;
- said illuminating device including at least three radiation transmitters for transmitting respective bundles of illuminating rays onto said surface, said radiation transmitters having respective illuminating optical axes with selected ones of said transmitters being mounted to cause the optical axes corresponding thereto to lie on said first conical surface while the remaining ones of said transmitters are mounted so as to cause the optical axes thereof to lie on said second conical surface; said first and second conical surfaces having a common vertex in the region of the surface of the sample and said transmitters conjointly defining an illuminated area (m) on the surface of the sample;
- said measuring device including a plurality of radiation receivers having respective receiving optical axes with selected ones of said receivers being mounted to cause the optical axes corresponding thereto to lie on said first conical surface while the remaining ones of said receivers are mounted so as to cause the optical axes thereof to lie on said second conical surface; each of said receivers including parallel beam means for receiving a bundle of parallel reflected rays from a core area (k) on said surface; and,
- said radiation transmitters including apeture means for limiting the bundle of said rays transmitted by said transmitters to an illuminated region (m) on said surface smaller than said core area (k) within said predetermined distance range (d).

* * * * *

UNITED STATES PATENT AND TRADEMARK OFFICE
CERTIFICATE OF CORRECTION

PATENT NO. : 4,919,535

DATED : April 24, 1990

INVENTOR(S) : Gerhard Hohberg and Hermann Gerlinger

It is certified that error appears in the above-identified patent and that said Letters Patent is hereby corrected as shown below:

In column 2, line 17: delete "repective" and substitute -- respective -- therefor.

In column 11, line 3, between "with" and "as", insert the following: -- said central axis and so --.

In column 11, line 4, between "an" and "area", insert the following: -- illuminated core --.

In column 14, line 16: delete "apeture" and substitute -- aperture -- therefor.

Signed and Sealed this

Twenty-third Day of July, 1991

Attest:

HARRY F. MANBECK, JR.

*Attesting Officer*      *Commissioner of Patents and Trademarks*